United States Patent
Lannert

[11] 3,940,424
[45] Feb. 24, 1976

[54] LACTONES
[75] Inventor: Kent P. Lannert, Freeburg, Ill.
[73] Assignee: Monsanto Company, St. Louis, Mo.
[22] Filed: Dec. 19, 1973
[21] Appl. No.: 426,295

[52] U.S. Cl............ 260/343.6; 252/89 R; 252/135; 252/141; 252/142; 252/156; 252/180; 252/542; 260/348 R; 260/348 A; 260/348 C; 260/514 H; 260/514 K; 260/521 P; 260/535 P; 260/343.3 R; 260/520 R
[51] Int. Cl.$^2$........................................ C07D 307/32
[58] Field of Search................................ 260/343.6

[56] References Cited
OTHER PUBLICATIONS
Garcia, Rev. Real Acad. Cienc. Exactas, Fis. Natur. Madrid 1973, 69(1), pp. 87–162, as cited in Chem Abstracts 115196s, 79, (1973).

Primary Examiner—Lorraine A. Weinberger
Assistant Examiner—Jane S. Myers
Attorney, Agent, or Firm—N. E. Willis; J. E. Maurer; T. N. Wallin

[57] ABSTRACT
Compounds represented by the formula

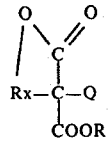

and salts thereof represented by the formula

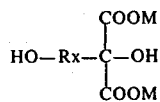

wherein Q is bromine, chlorine, —O-alkali metal or OH; R is hydrogen or an alkyl group containing from 1 to 20 carbon atoms; M is alkali metal; and Rx is

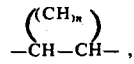

$n$ being an integer from 4 to 10, or

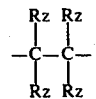

Rz being hydrogen, alkyl phenyl alkyl, alkoxy alkyl, alkoxy phenyl, alkoxy phenyl alkyl or —COOX, X being R or M, are useful as intermediates for the preparation of sequestrants.

4 Claims, No Drawings

LACTONES

BACKGROUND OF THE INVENTION

This invention relates to novel intermediates for preparation of hydroxy ether carboxylate salts useful as complexing agents and/or detergency builders.

The utility of compounds characterized by the ability to complex various metal and alkaline earth metal ions (particularly ions such as calcium ions which contribute to "hardness" of water) in aqueous media and/or provide, in combination with various detergent surfactants, detergent formulations of enhanced cleansing ability is well recognized by those skilled in the art. Such compounds are used in water treating applications (e.g. to "soften" water) and/or as detergency builders.

Although many compounds having complexing and/or detergency builder functionality are known, the provision of novel compounds composed of only carbon, hydrogen and oxygen and having such functionality is desirable as is the provision of intermediates for preparation of such compounds.

SUMMARY OF THE INVENTION

It is an object of this invention to provide novel intermediates for synthesis of compounds useful as complexing agents and/or detergency builders.

The compounds of this invention are esters and salts whose structure, synthesis, and use will be understood from the following description of the preferred embodiments.

DESCRIPTION OF THE PREFERRED EMBODIMENTS

The compounds of this invention are esters represented by the formula

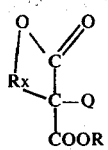

and salts thereof represented by the formula

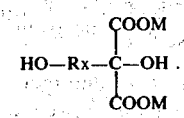

In the above formulae:

Q is bromine, chlorine, —O-alkali metal or —OH;
R is hydrogen or an alkyl group containing from 1 to 20 carbon atoms provided that when Q is —O-alkali metal, bromine or chlorine, R is an alkyl group.
M is alkali metal; and
Rx is

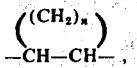

$n$ being an integer from 4 to 10, or

$Rz$ being hydrogen, alkyl, phenyl alkyl, alkoxy alkyl, alkoxy phenyl, alkoxy phenyl alkyl, or COOX, X being R in the cyclic compounds and M in their salts; and the total number of carbon atoms in Rx being from 2 to 22. The compounds wherein at least one of the Rz substituents on the carbon atom adjacent the cyclic oxygen or the hydroxy group is alkyl or, preferably, hydrogen, the remaining Rz substituents being hydrogen, are preferred.

To prepare the compounds of this invention, an epoxide of the formula

(The parenthetical "e" subscript is used to indicate that if Rx contains a COOX substituent, X will be alkyl, i.e., the ester form of the substituent.) is reacted with a malonic ester of the formula

wherein $R_1$ is an alkyl group containing from 1 to 20 carbon atoms.

Epoxides containing the Rx moiety desired for the compound being synthesized can be prepared by known techniques described, for example, in Weissberger, *Heterocyclic Compounds with Three and Four Membered Rings*, Part One, pages 1–523, (Interscience Publishers, 1964) and Maliworskii, *Epoxides and Their Derivatives* (Daniel Davey and Co., Inc., 1965) and the various references cited in these publications.

The reaction is conveniently conducted in a mutual solvent for the epoxide (I) and ester (II) which is not adversely reactive with these reactants or the reaction product (the alcohol corresponding to the ester (II) is generally satisfactory) at a temperature of from 0° to 60°C, preferably 40° to 45°C.

The reaction yields

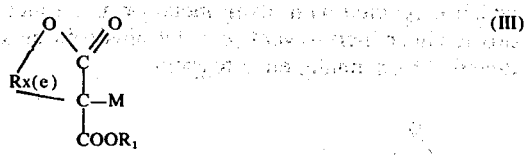

which is acidified (preferably with acetic acid) to yield

This compound (IV) is bromonated or chlorinated with elemental bromine or sulfuryl chloride to yield an ester of this invention.

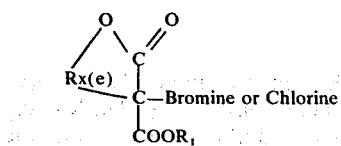 (V)

This ester (V) can be converted to another ester of the invention

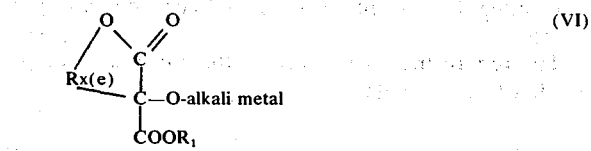 (VI)

by treatment with alkali metal hydroxide in an alcoholic or aqueous medium to yield the salt form of the compound

 (VII)

which is treated with a slight excess of sulfuric acid to form

 (VIII)

(Note: Any X in the Rx moiety will be hydrogen).
Esterification of compound (VIII) via conventional procedures yields

 (IX)

which is reacted with alkali metal or alkali metal hydroxide in an inert solvent (e.g., tetrahydrofuran, ether, dimethyl formamide, etc.) to yield

 (X)

The mechanism of epoxide ring opening in the reaction between (I) and (II) will favor formation of products wherein the Rz groups attached to the carbon atom adjacent to the heterocyclic oxygen (and, ultimately, the hydroxy group) are of larger spatial configuration than the Rz groups attached to the next carbon atom. However, mixtures of all possible products will be formed. Such mixtures may be utilized as such or separated by conventional techniques.

Those compounds of this invention encompassed by the formula

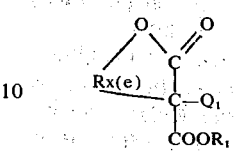

wherein $Q_1$ is bromine, chlorine or —O-alkali metal can be reacted with a compound represented by the formula

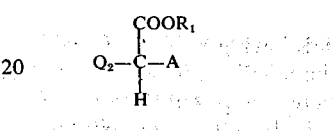

wherein A is hydrogen, methyl or ethyl and $Q_2$ is bromine or chlorine when $Q_1$ is —O-alkali metal and is —O-alkali metal when $Q_1$ is bromine or chlorine (The reaction is preferably conducted in a solvent for the non-cyclic ester, e.g., tetrahydrofuran, ether, dimethyl formamide, etc., which is not adversely reactive with the reactants or reaction products.) to yield

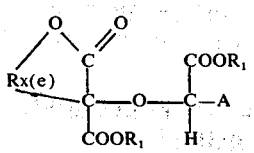

This later compound can be saponified by reaction with an alkali metal hydroxide to yield compounds represented by the formula

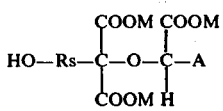

(Rs is the same as Rx except that in any —COOX substituents contained therein, X will be M instead of hydrogen or alkyl) which are useful as sequestrants and detergency builders.

These salts are, for example, used in detergent formulation which will contain at least 1% by weight and preferably at least 5% by weight of such salts. In order to obtain the maximum advantage the use of from 5% to 75% of these polycarboxylate salt compounds is preferred. The hydroxy ether polycarboxylate can be the sole detergency builder or these compounds can be utilized in combination with other detergency builders which may constitute from 0 to 95% by weight of the total builders in the formulation. By way of example, builders which can be employed in combination with the hydroxy ether polycarboxylate compounds include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, other ether polycarboxylates, alkyl polycarboxylates, epoxy polycarboxylates, tetrahydrofuran polycarboxylates such as 1,2,3,4 or 2,2,5,5 ) (tetrahydrofuran tetracarboxylates, benzene polycarboxylates, oxidized starches, amino (trimethylene phosphonic acid) and its salts, diphosphonic acids and salts (e.g. methylene diphosphonic acid; 1-hydroxy ethylidene diphosphonic acid) and the like.

The detergent formulations will generally contain from 5% to 95% by weight total builder (although greater or lesser quantities may be employed if desired) which, as indicated above, may be solely the hydroxy ether polycarboxylate salt compounds or mixtures of such compounds with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkyl sulfates and sulfonates; olefin sulfonates; alkenyl sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols; alkyl phenols, fatty acid amides, and fatty amines; amine oxides; sugar derivatives such as sucrose monopalmitate; long chain tertiary phosphine oxides; dialkyl sulfoxides; fatty acid amides, (e.g, mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecylammonio) propane-1-sulfonate and 3-(N,N-dimethyl-N-hexadecylammonio)-2-hydroxy propane-1-sulfonate.

Examples of suitable amphoteric surfactants include betains, sulfobetains and fatty acid imidazole carboxylates and sulfonates.

It will be understood that the above examples of surfactant are by no means comprehensive and that numerous other surfactants are known to those skilled in the art. It will be further understood that the choice and use of surfactants will be in accordance with well understood practices of detergent formulation. For example, anoinic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations 0.5% to 5%; liquid dishwashing formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brightners, soil antiredeposition agents, perfumes and the like.

In machine dishwashing compositions the surfactant will be a low-foaming nonionic or anionic, preferably nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40°C. The number of revolutions of the jet-spray arm during the wash and rinse cycles is counted. The results are compared with those obtained by operation of the machine using no surfactant charge, and the percentage decrease in number of revolutions is determined.

The surfactant should, of course, be compatible with the chlorine containing component hereinafter discussed. Examples of suitable nonionic surfactants include ethoxylated alkyl phenols, ethoxylated alcohols (both mono- and di- hydroxy alcohols), polyoxyalkylene glycols, aliphatic polyethers and the like. The widely commercially utilized condensates of polyoxypropylene glycols having molecular weights of from about 1,400 to 2,200 with ethylene oxide (the ethylene oxide constituting 5 to 35 weight percent of the condensate) are, for example, advantageously used in the machine dishwashing formulations of this invention.

Suitable low-foaming anionic surfactants include alkyldiphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro) tetra-(monopotassium dichloro)] penta-isocyanurate; (monotrichloro) (monopotassium dichloro) di-isocyanurate.

Machine dishwashing compositions should additionally contain from 5% to 30% soluble sodium silicate having an $SiO_2$ to $Na_2O$ mole ratio of from 1:1 to 3.2:1 preferably about 2.4:1 to inhibit corrosion of metal parts of dishwashing machines and provide overglaze protection to fine china.

Machine dishwashing compositions will generally contain at least 10%, preferably at least 20% builder, up to a maximum of about 90% builder. The new builder compounds of this invention should constitute at least 5% of the weight of the machine dishwashing formulation in order to obtain the full effects of their inherent characteristics.

The invention is further illustrated by the following examples, wherein all parts and percentages are by weight unless otherwise indicated.

EXAMPLE I

Metallic sodium (44 grams) is added to 900 ml. ethanol after which 320 grams of diethylmalonate is added to form an ethanol slurry of sodium diethylmalonate. A solution of 88 grams ethylene oxide in 300 ml. ethanol is added to the slurry, the temperature being maintained between 40° to 45°C, to form a slurry of

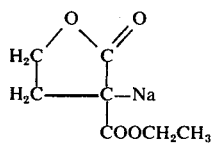

Following addition of the ethylene oxide, the slurry is stirred for 15 hours, at room temperature after which 120 ml. of glacial acetic acid is added to form

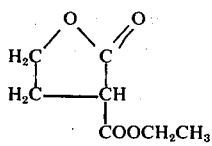

The ethanol is removed under reduced pressure, 500 ml. water is added to dissolve the sodium acetate and the organic phase is separated, dissolved in ether, washed with water, dried over $MgSO_4$—$CaSO_4$ and the ether evaporated.

Sixty-six grams of the

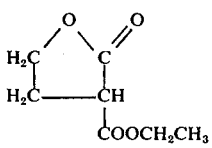

is dissolved in 75 ml. carbon tetrachloride and bromine added at reflux temperature to form

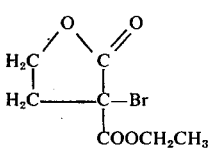

which is separated by evaporating the chloroform, dissolved in ether and washed with 5% $NaHCO_3$, saturated NaCl and water after which the ethereal solution is dried and the ether evaporated.

EXAMPLE II

Forty grams of ethyl glycolate in 50 ml. tetrahydrofuran is added to a slurry of about 8.6 grams sodium hydride in 300 ml. tetrahydrofuran and the mixture stirred for one hour at about 35°C to form a slurry of

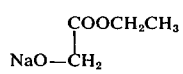

This slurry is cooled to about 10°C and a solution of 84 grams

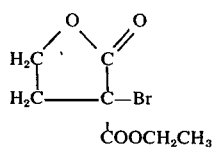

in 50 ml. tetrahydrofuran is added, the temperature being maintained at about 10°C. After one hour, the temperature is raised to 25°C and maintained at that level for 14 hours. The tetrahydrofuran is evaporated, the residue diluted with ether and washed with water, dried, and the ether evaporated. The residue is distilled, the product

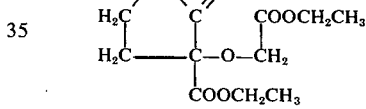

being collected at 123° to 125°C/0.1 mm. Hg.

A solution of 37 grams of

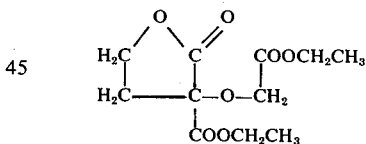

in 45 ml. ethanol is added slowly to 75 grams of an aqeuous 25% sodium hydroxide solution maintained below 40°C with an ice bath. The mixture is then stirred for about 4 hours at about 25°C and an aqueous solution of

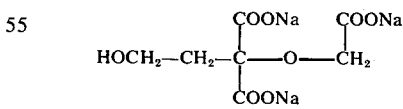

is separated. Successive washing with ethanol and acetone separates the salt as a solid product. This salt is tested for sequestration function using the procedures described by Matzner et al, "Organic Builder Salts as Replacements for Sodium Tripolyphosphate," *Tenside Detergents*, 10, Heft 3, pages 119–125 (1973). The sequestration value (intensity multiplied by capacity expressed as a percentage of sodium tripolyphosphate sequestration value) is 100%.

Detergent formulations containing 25%, 37.5% and 50%,

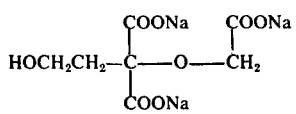

17% linear alkylbenzene sulfonate having an average molecular weight of about 230; 6% sodium silicate and a quantity of sodium sulfate sufficient to equal 100% are prepared. Those formulations are found to clean cotton and polyester/cotton fabrics substantially more effectively than otherwise identical compositions in which the

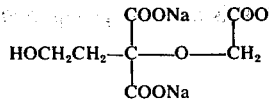

is replaced with a "filler," sodium sulfate.

EXAMPLE III

The compound

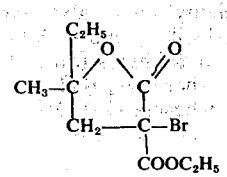

is prepared by reacting 86 grams of

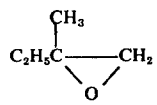

and 182 grams of

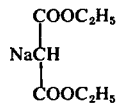

followed by acidification and bromination in accordance with the procedure of Example I. Stirring 140 grams of

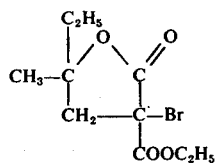

with 350 grams of 25% aqueous KOH at a temperature of 40° to 45°C for about 24 hours yields the salt

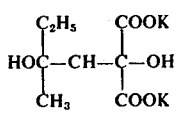

which is esterified to the hydroxy ester lactone

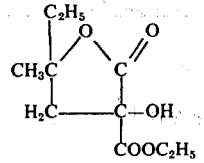

by conventional esterification techniques and purified by vacuum distillation.

Seventy-two grams of

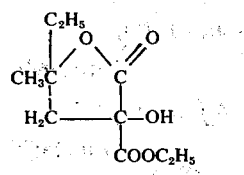

in 50 ml. tetrahydrofuran is added to a slurry of about 8.0 grams of sodium hydride in 300 ml. tetrahydrofuran and the mixture stirred for 1 hour at 30° to 35°C to form a slurry of

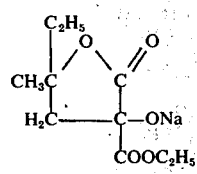

This slurry is cooled to about 10°C and a solution of 56 grams of ethyl bromoacetate in 50 ml. tetrahydrofuran is added, the temperature being maintained at about 10°C. After one hour, the temperature is raised to 25°C and maintained at that level for 18 hours. The tetrahydrofuran is evaporated, the residue diluted with ether and washed with water, dried, and the ether evaporated. The product,

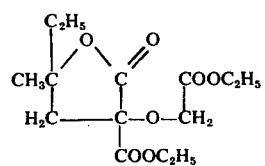

is purified by vacuum distillation.

Treatment of this ester with sodium hydroxide according to the procedures of Example II yields the salt

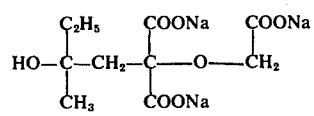

which is an effective sequestrant.

The preparation and use of other compounds of this invention will be apparent to those skilled in the art from the foregoing disclosure. For example, Table I below lists, in the first column, various epoxides from which compounds containing the Rx group shown in the second column are derived.

TABLE I

| Epoxide | Rx |
|---|---|
| 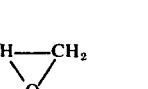 | 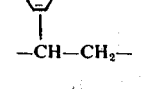 |
| 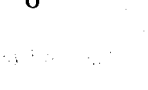 | 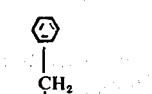 |
| 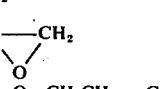 | 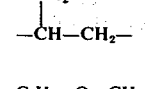 |
| 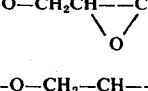 | 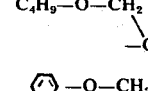 |
| 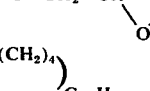 | 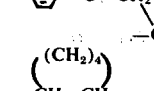 |
| 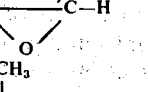 | 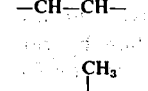 |
| 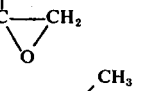 | 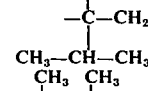 |
| 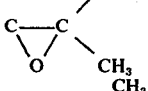 | 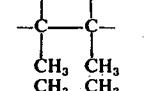 |

What is claimed is:
1. A compound represented by the formula

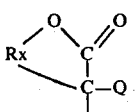

wherein:
Q is selected from the group consisting of bromine, chlorine, —O-alkali metal and —OH;
R is selected from the group consisting of hydrogen and alkyl groups containing from 1 to 20 carbon atoms, provided, that when Q is —O-alkali metal, bromine or chlorine, R is an alkyl group; and,
Rx is

Rz being hydrogen, alkyl, phenyl alkyl, alkoxy alkyl, alkoxy phenyl, alkoxy phenyl alkyl, and COOR; the total number of carbon atoms in Rx being from 2 to 22.
2. A compound of claim 1 wherein Q is Br.
3. A compound of claim 1 wherein Q is ONa.
4. A compound of claim 1 wherein Rx is

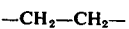

* * * * *

UNITED STATES PATENT OFFICE
CERTIFICATE OF CORRECTION

PATENT NO. : 3,940,424
DATED : February 24, 1976
INVENTOR(S) : Kent P. Lannert

It is certified that error appears in the above-identified patent and that said Letters Patent are hereby corrected as shown below:

In the Abstract, column 2, formula 3,

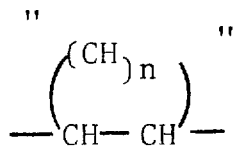

should be ---

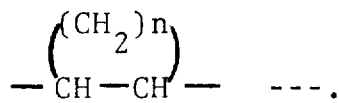 ---.

Signed and Sealed this eleventh Day of May 1976

[SEAL]

Attest:

RUTH C. MASON
Attesting Officer

C. MARSHALL DANN
Commissioner of Patents and Trademarks